(12) United States Patent
Vortman et al.

(10) Patent No.: US 12,728,293 B2
(45) Date of Patent: Sep. 8, 2026

(54) ULTRASOUND-MEDIATED NEUROSTIMULATION

(71) Applicant: INSIGHTEC, LTD., Tirat Carmel (IL)

(72) Inventors: Kobi Vortman, Haifa (IL); Shuki Vitek, Haifa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 442 days.

(21) Appl. No.: 17/267,858

(22) PCT Filed: Aug. 23, 2019

(86) PCT No.: PCT/IB2019/000941
§ 371 (c)(1),
(2) Date: Feb. 11, 2021

(87) PCT Pub. No.: WO2020/039257
PCT Pub. Date: Feb. 27, 2020

(65) Prior Publication Data
US 2021/0170205 A1 Jun. 10, 2021

Related U.S. Application Data

(60) Provisional application No. 62/722,509, filed on Aug. 24, 2018.

(51) Int. Cl.
*A61N 7/02* (2006.01)
*A61B 5/055* (2006.01)
(Continued)

(52) U.S. Cl.
CPC ................ *A61N 7/02* (2013.01); *A61B 5/055* (2013.01); *A61B 5/369* (2021.01);
(Continued)

(58) Field of Classification Search
CPC ........................................................ A61N 7/00
See application file for complete search history.

(56) References Cited

U.S. PATENT DOCUMENTS 6,613,005 B1 * 9/2003 Friedman ................ A61N 7/02 600/407
2011/0092800 A1 4/2011 Yoo et al.
(Continued)

FOREIGN PATENT DOCUMENTS

CN 102149428 A 8/2011

OTHER PUBLICATIONS

"Transcranial focused ultrasound stimulation of human primary visual cortex" by W. Lee et al. Scientific Reports. pp. 1-12, 2016 (Year: 2016).*
(Continued)

*Primary Examiner* — Jason M Ip
(74) *Attorney, Agent, or Firm* — Morgan, Lewis & Bockius LLP

(57) ABSTRACT

Various approaches to stimulating neural activity in one or more target regions associated with one or more brain diseases or disorders include transmitting the first sequence of ultrasound pulses to the target region(s); measuring a physiological parameter indicative of the neural activity at the target region(s) resulting from the ultrasound pulses; and based at least in part on the measurement, adjusting a parameter value associated with one or more transducer elements so as to achieve a target objective of the neural activity.

21 Claims, 7 Drawing Sheets

(51) Int. Cl.
*A61B 5/369* (2021.01)
*A61N 7/00* (2006.01)

(52) U.S. Cl.
CPC ................. *A61N 2007/0021* (2013.01); *A61N 2007/0095* (2013.01); *A61N 2007/027* (2013.01)

(56) References Cited

U.S. PATENT DOCUMENTS

2013/0184728 A1 7/2013 Mishelevich
2014/0058292 A1 2/2014 Alford et al.
2015/0151142 A1 6/2015 Tyler et al.
2015/0359603 A1* 12/2015 Levy ........................ A61N 7/02 703/2
2016/0008620 A1* 1/2016 Stubbeman ........ A61N 1/36082 607/45
2016/0008633 A1 1/2016 Vortman et al.
2016/0303402 A1 10/2016 Tyler
2018/0236255 A1* 8/2018 Etkin .................. A61B 5/4836

OTHER PUBLICATIONS

"Focused ultrasound modulates region-specific brain activity" by S. Yoo et al. NeuroImage. 56, pp. 1267-1275, 2011 (Year: 2011).*
International Search Report & Written Opinion, PCT Application No. PCT/IB2019/000941, dated Dec. 13, 2019, 13 pages.
Office Action issued in the corresponding Chinese Application No. 201980070248.6 dated Aug. 26, 2023, with English Translation.

* cited by examiner

ULTRASOUND-MEDIATED NEUROSTIMULATION

CROSS-REFERENCE TO RELATED APPLICATION

This application is a U.S. National Phase Application of PCT/IB2019/000941, filed Aug. 23, 2019, which claims priority to and the benefits of U.S. Provisional Patent Application No. 62/722,509, which was filed on Aug. 24, 2018. The entire disclosures of these priority documents are hereby incorporated by reference in their entireties.

FIELD OF THE INVENTION

The present invention relates, generally, to systems and methods for neurostimulation and, more particularly, to neurostimulation using focused ultrasound.

BACKGROUND

Deep brain stimulation (DBS) is a neurosurgical procedure in which electrical impulses are sent to specific disease- or disorder-related targets in the brain. These signals regulate abnormal impulses or beneficially affect certain cells and chemicals within the brain, thereby alleviating neurological diseases or disorders (e.g., tremor, Parkinson's disease, dystonia, and obsessive-compulsive disorder). Typically, DBS involves implantation of a neurostimulator having three medical components—a pulse generator (IPG) implanted in the patient's chest for controlling the electrical impulses, four electrodes situated in one or two nuclei of the patient's brain for delivering the impulses thereto, and extensions connecting the electrodes to the IPG. Neurostimulator implantation, however, requires surgery, which can be painful and can create a risk of infection. In addition, the neurostimulator may need to be replaced when the battery depletes or if the device malfunctions.

Further, once implanted, the electrodes stimulate at most two regions at fixed locations of the brain. It may, however, be desirable to stimulate more regions associated with the disease/disorder so as to increase treatment efficacy. Additionally, the patient may exhibit multiple diseases/disorders that require brain stimulation at more than two regions for effective treatment. As a result, there is a need for a noninvasive approach that facilitates brain stimulation at multiple (e.g., more than two) target locations with the ability to change the stimulated locations if desired.

DESCRIPTION

The present invention provides systems and methods for noninvasively stimulating multiple (e.g., more than two) regions of the brain using transcranial focused ultrasound (i.e., acoustic waves having a frequency greater than about 20 kiloHertz) applied by an ultrasound transducer array. The transducer array may include multiple transducer elements that are "tiled" to form a flat or curved surface; by driving different elements with different phases of a driver signal, beams from the elements may be directed to a target region and collectively converge to a focus. Acoustic pressure at the focus, provided at a low intensity that does not cause clinically significant temperature elevation, may effectively modulate the excitability and stimulate the sonicated region of the brain with high spatial selectivity. As a result, multiple sonication sessions (e.g., one hour per week for four weeks) may affect the target region (e.g., regulation of electric impulses, change in certain cells or chemicals therein, etc.) in a manner comparable to conventional neurostimulators (e.g., IPG and implanted electrodes).

In various embodiments, relative phases of the acoustic waves or pulses emitted from the transducer elements are dynamically adjusted to steer the acoustic beam's focus. This allows the ultrasound-mediated neurostimulation to be applied to multiple regions (e.g., multiple sub-regions within a target region or multiple target regions) if desired. In addition, the transducer elements may be grouped into multiple sub-arrays; settings (e.g., relative phases, frequencies and/or amplitudes) of the transducer elements in each sub-array can be independently and separately determined so as to create a focus at a desired brain region. Accordingly, the sub-arrays can generate multiple foci to substantially simultaneously or sequentially (having very short delays) stimulate multiple regions in the brain. This approach may advantageously increase the stimulated volume of the brain region specific to a disease/disorder, thereby enhancing treatment efficacy. Alternatively, this approach may allow multiple brain regions related to different diseases/disorders to be stimulated during the same ultrasound procedure, thereby enabling simultaneous treatment of multiple diseases/disorders.

In various embodiments, neural activities or other treatment effects of the sonicated brain region(s) are monitored in real time using a measuring system (such as functional magnetic resonance imaging (fMRI) and/or electroencephalography (EEG)) during the ultrasound-mediated neurostimulation. The settings of the transducer elements may then be adjusted based on the real-time feedback so as to ensure that a target treatment objective (e.g., a desired change in the blood flow) is achieved.

Accordingly, various embodiments provide noninvasive, focused-ultrasound-mediated neurostimulation that allows multiple (e.g., more than two) target regions to be substantially simultaneously or sequentially stimulated for treatment. In addition, by monitoring the neural activity of the target region(s) during application of the ultrasound and, based thereon, providing real-time feedback for sonication adjustment, effective and efficient treatment may be achieved.

Accordingly, in one aspect, the invention pertains to a system for stimulating neural activity in one or more target regions associated with one or more brain diseases or disorders using focused ultrasound. In various embodiments, the system includes an ultrasound transducer having multiple transducer elements; and a controller configured to (a) transmit the first sequence of ultrasound pulses/bursts to the target region; (b) cause measurements of a physiological parameter (e.g., a change in a blood flow or a change in a chemical in tissue at the target region(s)) indicative of the neural activity at the target region(s) resulting from the ultrasound pulses/bursts; and (c) based at least in part on the measurements, adjust the first parameter value (e.g., a frequency, a phase, an amplitude and/or a transducer activation duration) associated with one or more transducer elements so as to achieve a target objective of the neural activity. In one implementation, the system further includes a monitoring system (e.g., a fMRI, ASL MRI, EEG and/or fNIRS) for measuring the physiological parameter at the target region(s).

In addition, the controller is further configured to cause the sequence of ultrasound pulses/bursts to create a focus at the target region(s); cause measurements of a temperature at the focus; and based at least in part on the measured temperature, adjust the second parameter value (e.g., a frequency, a phase, an amplitude and/or an activation duration) associated with the transducer element(s) to avoid damage to the target region(s). In one embodiment, the controller is further configured to cause steering of the focus at multiple sub-regions of the target region. In another embodiment, the controller is further configured to cause sequential steering of the focus at multiple target regions, each associated with a brain disease or disorder, different target regions associated with different brain diseases or disorders.

In some embodiments, the ultrasound transducer includes multiple sub-arrays, each sub-array having multiple transducer elements. The controller may be further configured to cause the first and second different sub-arrays of the transducer to sequentially or substantially simultaneously transmit multiple ultrasound pulse sequences to the first and second different sub-regions, respectively, of the target region. Additionally or alternatively, the controller may be further configured to cause the first and second different sub-arrays of the transducer to sequentially or substantially simultaneously transmit multiple ultrasound pulse sequences to the first and second different target regions, respectively; the first and second target regions are associated with different brain diseases or disorders. In some embodiments, the controller is further configured to compare the measured physiological parameter against the target objective; and repeat steps (a)-(c) until the target objective is satisfied.

In another aspect, the invention relates to a method of stimulating neural activity in one or more target regions associated with one or more brain diseases or disorders. In various embodiments, the method includes transmitting the first sequence of ultrasound pulses/bursts from an ultrasound transducer having multiple transducer elements to the target region(s); measuring a physiological parameter (e.g., e.g., a change in a blood flow or a change in a chemical in tissue at the target region(s)) indicative of the neural activity at the target region(s) resulting from the ultrasound pulses/bursts; and based at least in part on the measurement, adjusting a parameter value (e.g., e.g., a frequency, a phase, an amplitude and/or a transducer activation duration) associated with one or more the transducer elements so as to achieve a target objective of the neural activity. In one implementation, the method further includes causing the sequence of ultrasound pulses/bursts to create a focus at the target region(s); causing measurements of a temperature at the focus; and based at least in part on the measured temperature, adjusting the second parameter value (e.g., a frequency, a phase, an amplitude and/or an activation duration) associated with the transducer element(s) to avoid damage to the target region (s).

In various embodiments, the ultrasound transducer includes multiple sub-arrays, each sub-array having multiple transducer elements; the method further includes causing the first and second different sub-arrays of the transducer to sequentially or substantially simultaneously transmit multiple ultrasound pulse sequences to the first and second different sub-regions, respectively, of the target region. Additionally or alternatively, the method further includes causing the first and second different sub-arrays of the transducer to sequentially or substantially simultaneously transmit multiple ultrasound pulse sequences to the first and second different target regions, respectively; the first and second target regions are associated with different brain diseases or disorders.

As used herein, the term "clinically significant" means having an undesired (and sometimes the lack of a desired) effect on tissue that is considered significant by clinicians, e.g., prior to triggering the onset of damage thereto. In addition, the terms "approximately," "roughly," "sufficiently," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
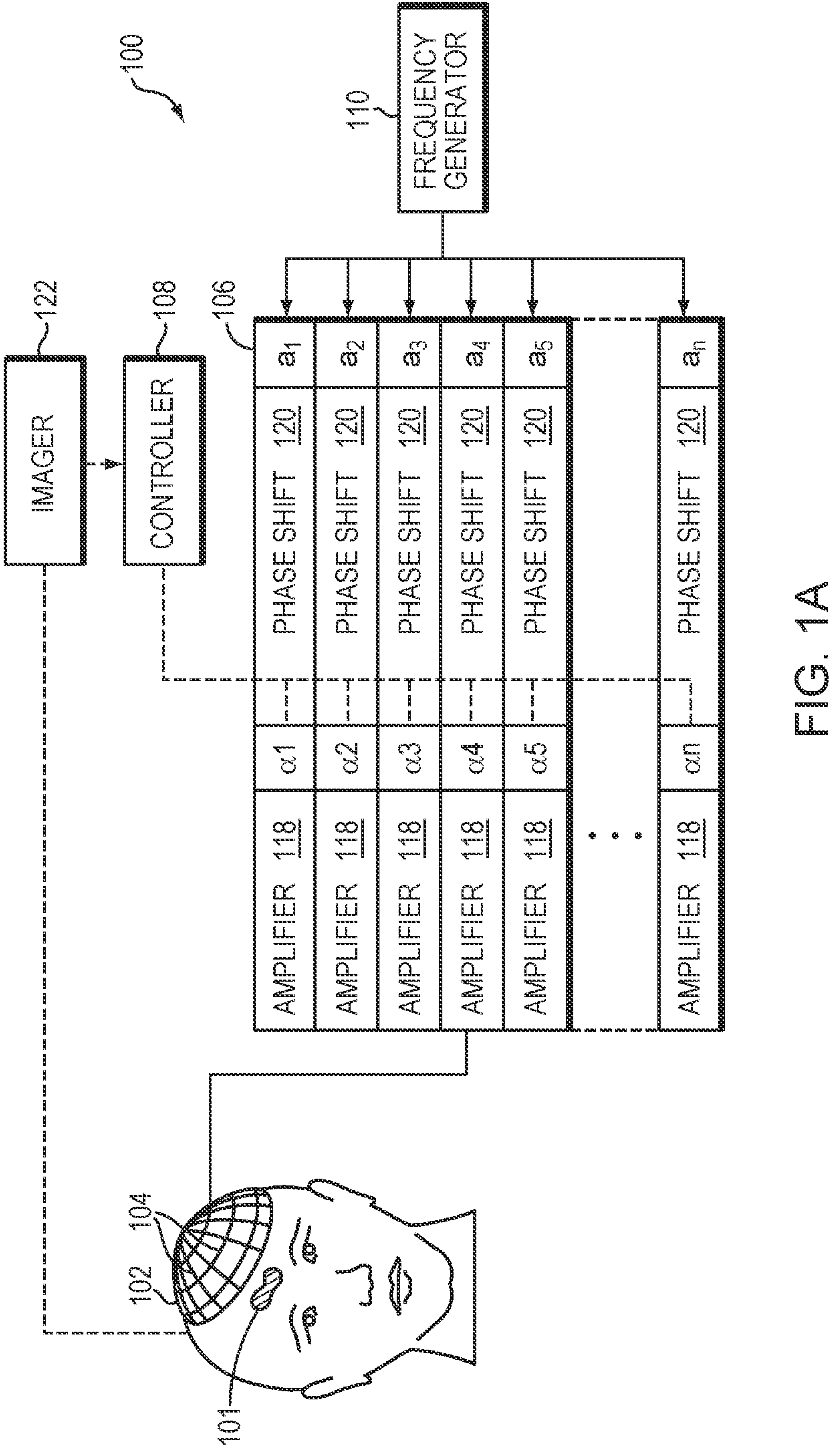
FIG. 1A schematically depicts an exemplary ultrasound system in accordance with various embodiments of the current invention.

FIG. 1A illustrates an exemplary ultrasound system 100 for generating and delivering a focused acoustic energy beam to a target region 101 in the patient's brain for stimulating neural activities therein and thereby treating a neurological disease or disorder. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for surrounding the patient's head, or may include one or more planar or otherwise shaped sections. Its dimensions may vary between millimeters and tens of centimeters. The transducer elements 104 of the array 102 may be made, for example, of piezoelectric ceramics, piezo-composite materials, or generally any materials using any techniques capable of converting electrical energy to acoustic energy, and may be mounted in silicone rubber or another material (including air) suitable for damping the mechanical coupling between the elements 104. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase/time delay circuit 120; each drive circuit drives one of the transducer elements 104. The beamformer 106 receives a radiofrequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radiofrequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $\alpha_1$-$\alpha_n$ imposed by the beamformer 106 serve to transmit and focus ultrasonic energy onto the target region 101, and account for wave distortions induced in the tissue located between the transducer elements 104 and the target region 101. Approaches to compensating for beam aberrations resulting from the intervening tissue and generating a focus having desired properties at a desired location are provided, for example, in International Application No. PCT/IB32017/000990, filed on Jul. 19, 2017, the entire disclosure of which is hereby incorporated by reference.

The amplification factors and phase shifts are computed by the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial acoustic field patterns at the target region 101. In certain embodiments, the computation is based on detailed information about the characteristics (e.g., structure, thickness, density, etc.) of the tissue located between the transducer element 104 and their effects on propagation of acoustic energy. Such information may be obtained from an imager 122. The imager 122 may be, for example, a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 122 may provide a set of two-dimensional (2D) images suitable for reconstructing a three-dimensional image of the target region and/or its surrounding region(s). The imager 122 may be operated using the same controller 108 that facilitates the transducer operation; alternatively, it may be separately controlled by a separate controller intercommunicating with the controller 108.

In some embodiments, the transducer array 102 may be configured to mechanically or electrically generate an ultrasound steering beam so as to sequentially stimulate multiple target regions or multiple sub-regions within a target region. This may advantageously increase the stimulated volume of the regions specific to a disease/disorder, thereby enhancing treatment efficacy thereof. Additionally or alternatively, this approach may enable various brain regions related to different diseases/disorders to be stimulated, thereby providing treatment to multiple diseases/disorders in the same procedure. In one embodiment, the transducer elements 104 are steered mechanically, i.e., physically moved with respect to the target region(s). Mechanical steering is particularly suitable when the transducer array 102 is substantially larger than the skull (e.g., about 30 cm or more in diameter) to provide sufficient freedom of movement. Alternatively, the beam may be steered electronically by adjusting the relative phases of the acoustic waves/pulses emitted from the transducer elements 104. The degree of control provided by such electronic steering is inversely proportional to the size of the individual transducer elements 104. For example, it is generally desirable to have the size of the transducer elements 104 be on the order of the wavelength of the acoustic energy emitted by the array, and preferably as small as half the wavelength, in order to effectively steer the ultrasound beams. Thus, with acoustic energy having a wavelength on the order of two millimeters (2 mm), as is often used for focused ultrasound systems, transducer elements 104 having a similar size, i.e., about 2 mm or less in cross-section, would be needed for effective steering. Electronic steering is preferred since physical movement of the transducer array 102 is not required and steering occurs quickly.

Figure 1B:
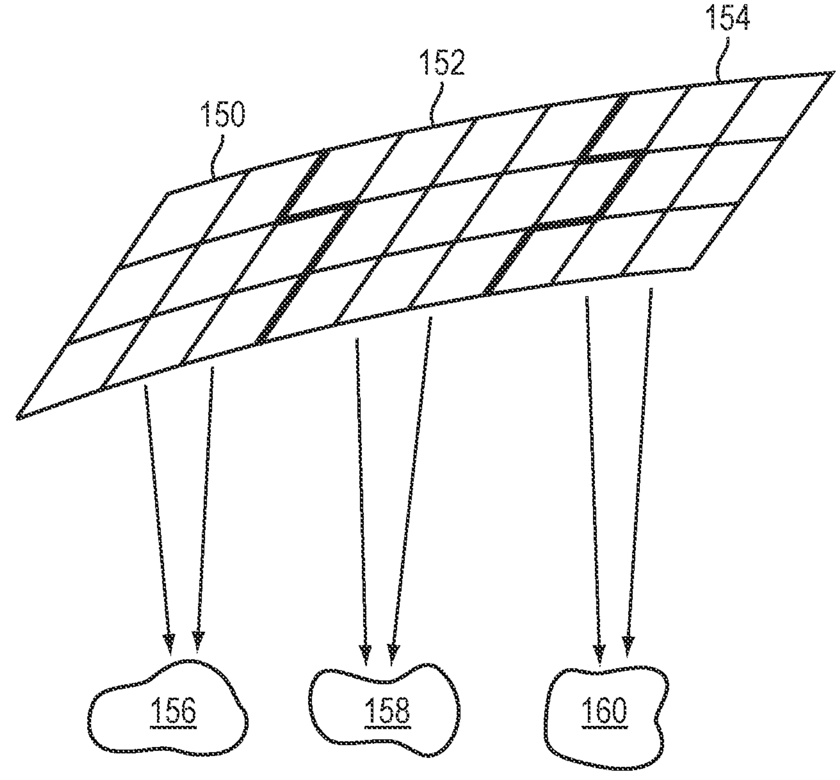
FIG. 1B depicts an exemplary configuration of the transducer elements for generating multiple foci at multiple target regions in accordance with various embodiments.
Figure 1C:
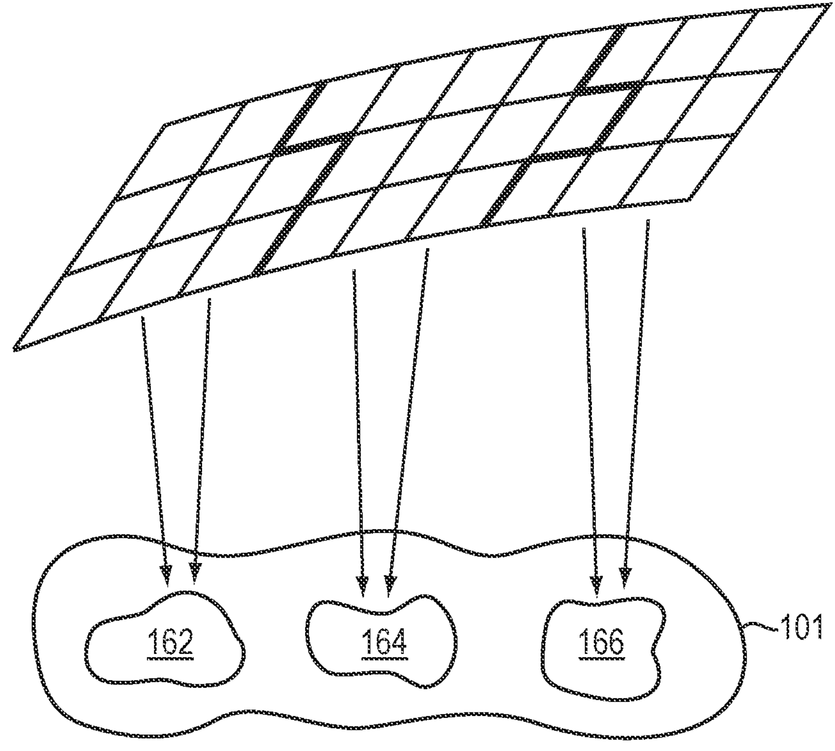
FIG. 1C depicts an exemplary configuration of the transducer elements for generating multiple foci at multiple sub-regions within a target region in accordance with various embodiments.

In some embodiments, the transducer array 102 is configured to generate multiple foci substantially simultaneously. For example, referring to FIG. 1B, the controller 108 may dynamically group the transducer elements 104 into multiple sub-arrays 150-154; each sub-array comprises or consists of a one- or two-dimensional array (i.e., a row or a matrix) of transducer elements 104. The transducer sub-arrays 150-154 may be separately controllable, i.e., they are each capable of emitting ultrasound waves at frequencies, amplitudes and/or phases that are independent of the frequencies, amplitudes and/or phases of the other sub-arrays. For example, each sub-array may create a focus on one of the target regions 156-160 by adjusting the relative phases of the elements 104 therein. As a result, multiple target regions 156-160 may be subsequently or substantially simultaneously stimulated by the focused ultrasound. Likewise, referring to FIG. 1C, each sub-array may be independently controlled to create a focus on one of the sub-regions 162-166 within a single target region. Groupings of the sub-arrays 150-154 may be dynamically determined by one or more targeting criteria that specify the geometric relationships among the elements 104 and/or between the elements 104 and the sub-regions/target regions (e.g., steering angles and/or lines of sight). The targeting criteria may also consider the physical locations of the sub-regions/target regions, the number of sub-regions/target regions, anatomical features of the tissue intervening the sub-regions/target regions and the elements 104, etc. It should be noted that the configurations of the transducer sub-arrays provided herein are for illustration only, and the present invention is not limited to such configurations. One of ordinary skill in the art will understand that many variations are possible and are thus within the scope of the present invention.

Figure 2:
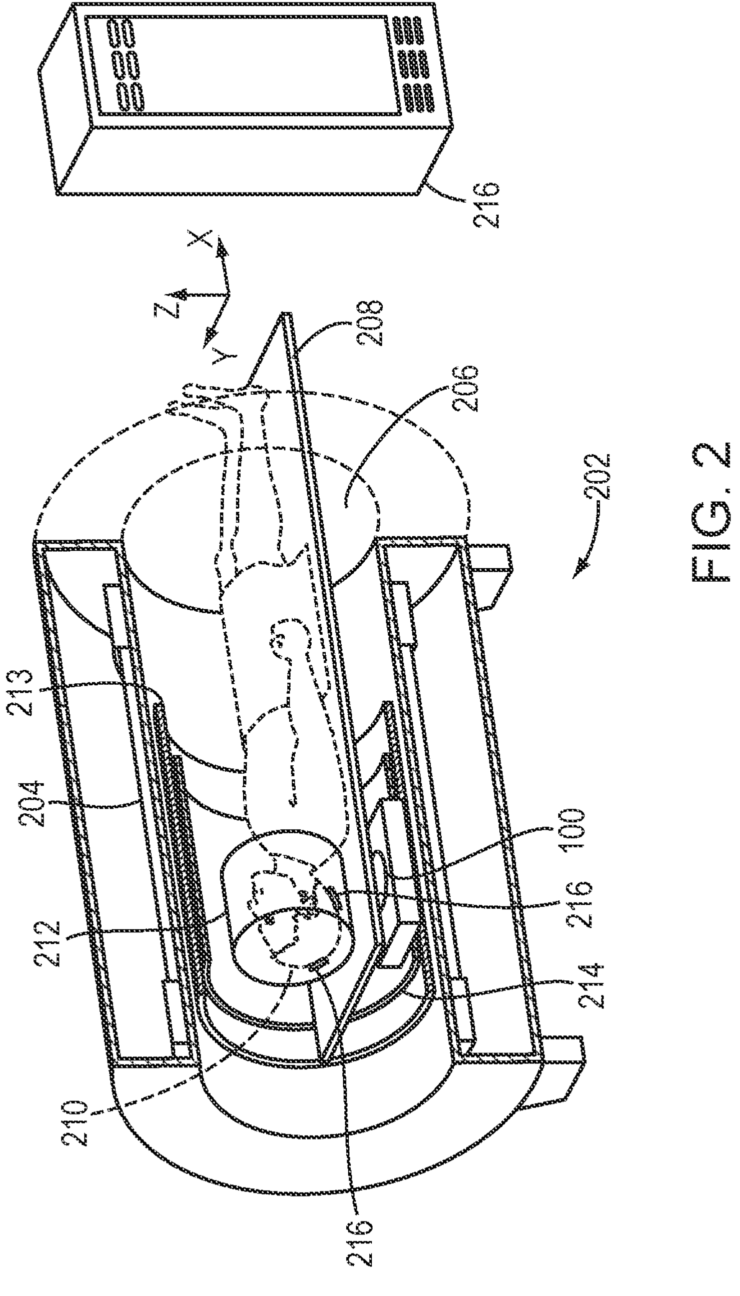
FIG. 2 schematically depicts an exemplary MRI system in accordance with various embodiments of the current invention.

To perform the ultrasound-mediated neurostimulation, it is necessary to determine the location of the target region(s) with precision prior to the ultrasound procedure. Accordingly, in various embodiments, the imager 122 is first activated to acquire images of the target region(s) and, in some cases, the surrounding non-target region(s). For example, a tissue volume may be represented as a 3D set of voxels (i.e., volumetric pixels) based on a 3D image or a series of 2D image slices and may include the target region(s) and/or non-target region(s). FIG. 2 illustrates an exemplary imager—namely, an MRI apparatus 202. The apparatus 202 may include a cylindrical electromagnet 204, which generates the requisite static magnetic field within a bore 206 of the electromagnet 204. During medical procedures, the patient is placed inside the bore 206 on a movable support cradle 208. A region of interest 210 within the patient (e.g., the patient's head) may be positioned within an imaging region 212 where the electromagnet 204 generates a substantially homogeneous field. A set of cylindrical magnetic field gradient coils 213 may also be provided within the bore 206 and surrounding the patient. The gradient coils 213 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 214 surrounding the imaging region 212 emits RF pulses into the imaging region 212 to cause the patient's tissues to emit magnetic-resonance (MR) response signals. Raw MR response signals are sensed by the RF coil 214 and passed to an MR controller 216 that then computes an MR image, which may be displayed to the user. Alternatively, separate MR transmitter and receiver coils may be used. Images acquired using the MRI apparatus 202 may provide radiologists and physicians with a visual contrast between different tissues and detailed internal views of a patient's anatomy that cannot be visualized with conventional x-ray technology. The acquired images are then analyzed by a controller that implements conventional image-analysis software to determine the location and/or anatomic characteristics (e.g., type, property, structure, thickness, density, etc.) of the target/non-target tissue.

The MRI controller 216 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the target region to be stimulated is identified. The image-processing system may be part of the MRI controller 216, or may be a separate device (e.g., a general-purpose computer containing image-processing software) in communication with the MRI controller 216.

In some embodiments, the focused ultrasound transducer system 100 is disposed within the bore 206 of the MRI apparatus 202. In addition, the ultrasound system 100 may include MR tracking coils or other markers for determining the transducer position and orientation relative to the target region in the MR image. Based on computations of the required transducer element phases and amplitudes, the transducer array is driven so as to focus ultrasound at the target.

In various embodiments, the MRI apparatus 202 is utilized in conjunction with a blood oxygen level-dependent (BOLD) contrast agent for detecting changes in the blood flow at the target/non-target region(s) in real time (this technique is often termed "functional magnetic resonance imaging" or "fMRI") during the ultrasound-mediated stimulation. Typically, when the target region is stimulated, the neural activity therein increases, which then causes additional blood to be oxygenated, thereby generating a change in the blood flow. The blood flow change may result in a BOLD signal change that can be detected by fMRI. Accordingly, fMRI may provide feedback to the stimulation effects on the target/non-target region(s) upon application of the ultrasound.

Figure 3A:
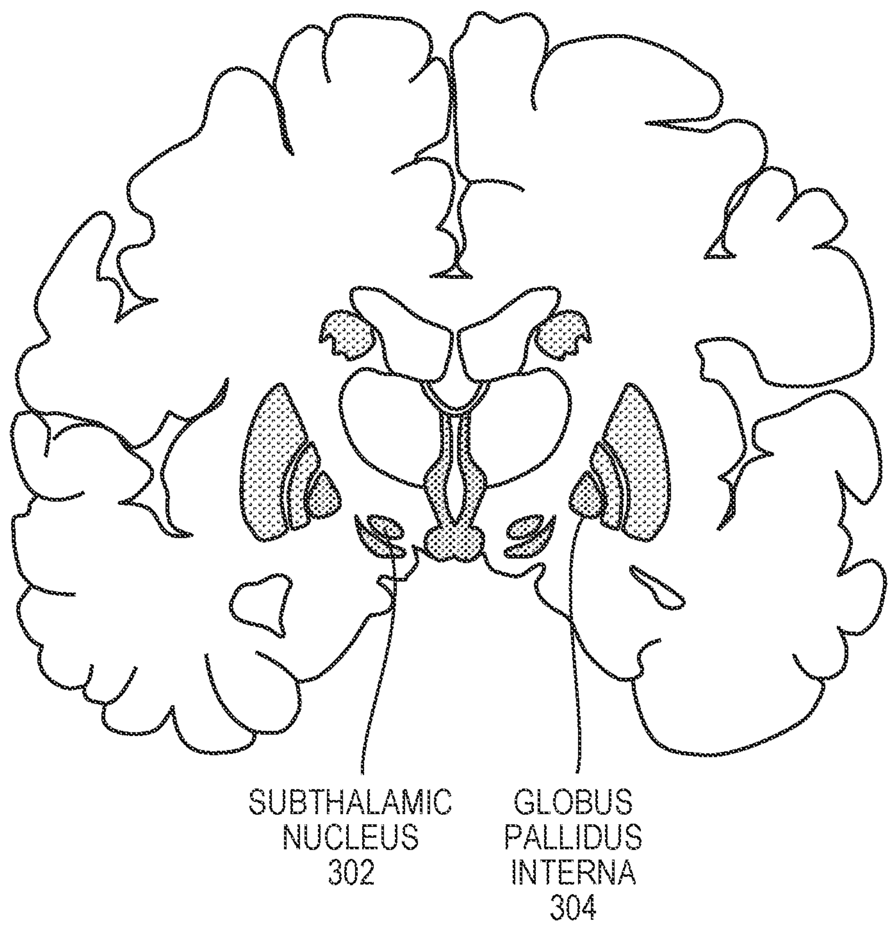
FIG. 3A depicts one or more brain regions that are stimulated by ultrasound waves/pulses for treating one or more brain diseases/disorders in accordance with various embodiments.
Figure 3B:
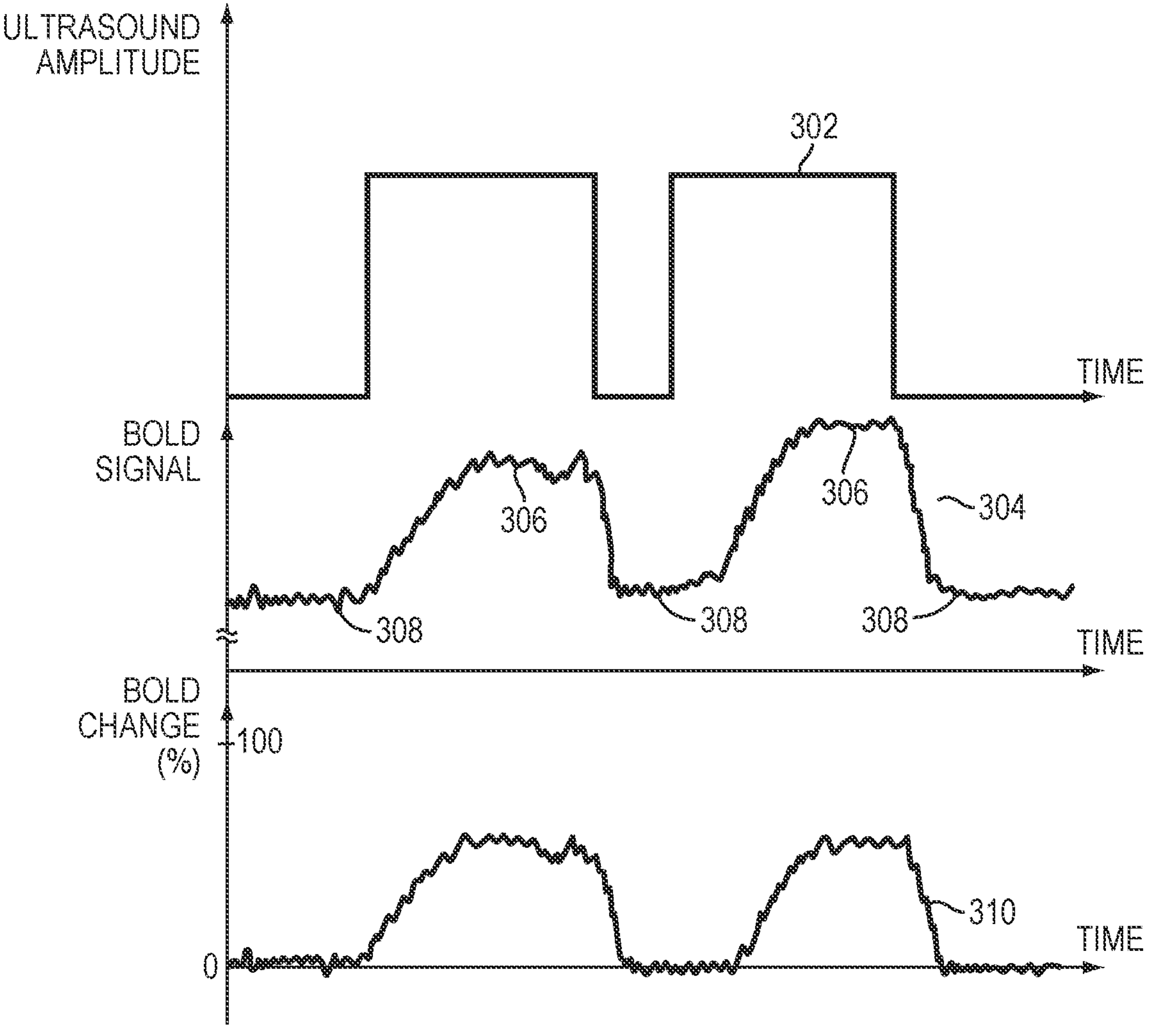
FIG. 3B depicts application of ultrasound pulses/waves to a target region and measurements of tissue in the target region in response to the ultrasound application in accordance with various embodiments.

For example, referring to FIG. 3A, to treat Parkinson's disease, the focused ultrasound may be applied to one or more specific target regions (e.g., the subthalamic nucleus 302 and/or the globus pallidus interna 304). The fMRI may be activated to acquire an image of the regions where the blood flow has increased during the ultrasound procedure. The image may be utilized to verify that the neural activity in the target region has been stimulated sufficiently to cause a change (e.g., more than 10%) in the blood flow, while the neural activity in the non-target region remains sufficiently unchanged (e.g., less than 5%) to avoid undesired effects. In addition, the BOLD signals may be analyzed to determine whether the strength of the stimulation achieves a desired objective. For example, prior to application of the focused ultrasound, the change in the BOLD signals at the target region resulting from deep brain stimulation that successfully treats Parkinson's disease may be first acquired, for example, from known literature; and this BOLD signal change may be stored in memory and set as the target object for the ultrasound treatment. Referring to FIG. 3B, during application of a sequence 302 of the ultrasound pulses/waves to the target, the BOLD signals 304 at the target may be measured in real time. As depicted, the amplitudes of the BOLD signals 306 during the sonications are larger than those of the BOLD signals 308 measured between two sonication pulses/waves/bursts. Thus, in one embodiment, the amplitudes of the BOLD signals 308 between two pulses/waves/bursts are first averaged to obtain a baseline level; the amplitudes of the BOLD signals 306 during sonications are then compared against the baseline level to determine the change 310 therebetween. The measured BOLD change 310 may then be compared against the target objective determined, e.g., from the literature, as described above. If the measured BOLD change is smaller than the target objective, the amplitude, frequency and/or duration of the sonication in the succeeding pulses may be increased. Alternatively, the ultrasound focus may be directed to a different sub-region of the target (e.g., in some embodiments, in the course of continuously steering between different sub-regions of the target); this may effectively increase the change in BOLD signals at the target region, thereby achieving the desired objective.

If the measured BOLD change at the target region and/or non-target region is larger than the target objective, the amplitude and/or duration of the sonication in the succeeding pulses may remain unchanged or, in some embodiments, reduced to ensure safety. It should be stressed, of course, that this exemplary use of fMRI for adjusting the ultrasound amplitudes and/or application durations is for illustrative purposes only, and that any signals indicative of physiological conditions related to the neural activities may be used as feedback to adjust any ultrasound parameters (e.g., amplitude, activation and deactivation, frequency, steering angle, etc.) as appropriate to the application.

In some embodiments, the temperature of the target region during the sonications is monitored in real time using, for example, the MRI apparatus 202, in order to avoid damage thereto. Based on the measured temperature, the relative phases and/or amplitudes of the ultrasound waves/pulses emitted from the elements 104 may be adjusted such that the temperature elevation resulting from the acoustic energy at the focus does not exceed a predetermined threshold. Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method exploits the phenomenon that the MR resonance frequency of protons in water molecules changes linearly with temperature. Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after or during the temperature change, thereby capturing a small phase change that is proportional to the change in temperature. A map of temperature changes may then be computed from the MR images by determining, on a voxel-by-voxel basis, phase differences between the baseline image and the treatment image, and converting the phase differences into temperature differences based on the PRF temperature dependence while taking into account imaging parameters such as the strength of the static magnetic field (in general 1.5 T or 3 T) and echo time (TE) (e.g., of a gradient-recalled echo). Various alternative or advanced methods may be used to compensate for patient motion, magnetic-field drifts, and other factors that affect the accuracy of PRF-based temperature measurements; suitable methods known to those of skill in the art include, e.g., multibaseline and referenceless thermometry, and are implemented without undue experimentation.

Additionally or alternatively, arterial spin labeling (ASL) MRI that uses magnetically labeled arterial-blood water protons as an endogenous tracer may be implemented to directly measure the blood flow change. The arterial blood water may be magnetically labeled by applying an RF pulse that inverts or saturates the water protons in the flowing blood supplying the imaged target/non-target regions. After a period of delay time, the labeled blood flows into the imaged region; the inflowing inverted spins within the labeled blood water may alter total tissue magnetization and, consequently, the MR signal and image intensity. During this time, the MR signal and image (called the tag image) may be acquired. By subtracting the tag image from the control image (where no arterial blood is labeled), the amount of arterial blood delivered to each voxel within the target/non-target regions within the transit time can be determined. This approach thus allows the ASL (arterial spin labeling) to qualitatively measure the blood flow change resulting from the ultrasound-mediated stimulation.

Similar to measurements of the BOLD signals described above, the amplitude of ASL signals at the target region corresponding to effective treatment resulting from conventional deep brain stimulation may be acquired prior to the ultrasound procedure; this amplitude is set as the target objective. During the sonications, the ASL signals at the target region can be measured in real time and compared against the target objective. Again, if the amplitude of the measured ASL signals is smaller than the target objective, the amplitudes and/or durations of the sonications in the next pulses may be increased. Additionally or alternatively, the ultrasound focus may be directed to a different sub-region of the target (e.g., in some embodiments, in the course of steering between different sub-regions of the target region as described above) to enhance the neural activity, and thereby enhance ASL signals. If the measured ASL signals at the target region are larger than the target objective, the amplitudes and/or durations of the sonications may remain unchanged or, in some embodiments, reduced to ensure safety.

The fMRI and/or ASL may be combined with other measures of brain physiology. For example, referring again to FIG. 2, multiple electrodes 216 may be placed along the patient's scalp to monitor the electrical activity of the brain (this technique is often termed "electroencephalograph" or "EEG") during the ultrasound-mediated neurostimulation. Alternatively, functional near-infrared spectroscopy (fNIRS) may be employed. Once again, the EEG signals, fNIRS signals, alone or in combination with fMRI and/or ASL, may be compared against a target objective determined using other approaches (e.g., conventional deep brain stimulation); and based thereon, the ultrasound parameters (e.g., the amplitudes, application durations, phases, frequencies, steering angles, etc.) may be adjusted to ensure treatment efficacy and safety. In some embodiments, these feedback signals are utilized to determine whether to sequentially or substantially simultaneously stimulate multiple sub-regions of the target and/or multiple target regions as described above.

Generally, the ultrasound-mediated neurostimulation may effectively treat the diseases/disorders after a few sessions (e.g., one hour per week for four weeks) (although, in some embodiments, more sessions of the sonications may be required); this approach thus advantageously obviates the need for invasive implantation of the neurostimulator required by the conventional approach to deep brain stimulation. In addition, by adjustment of the relative phases of the acoustic waves/pulses emitted from the transducer elements, the focused ultrasound beam may be dynamically steered to various locations of one or more target regions. This may increase the treatment efficacy of one disease/disorder or enable multiple diseases/disorders to be treated in the same procedure. Further, by grouping the transducer elements into multiple sub-arrays, multiple sub-regions of a target and/or multiple target regions can be stimulated substantially simultaneously or sequentially. Again, this approach may advantageously enhance treatment efficacy and/or allow different diseases/disorders to be treated during the same ultrasound procedure.

Figure 4:
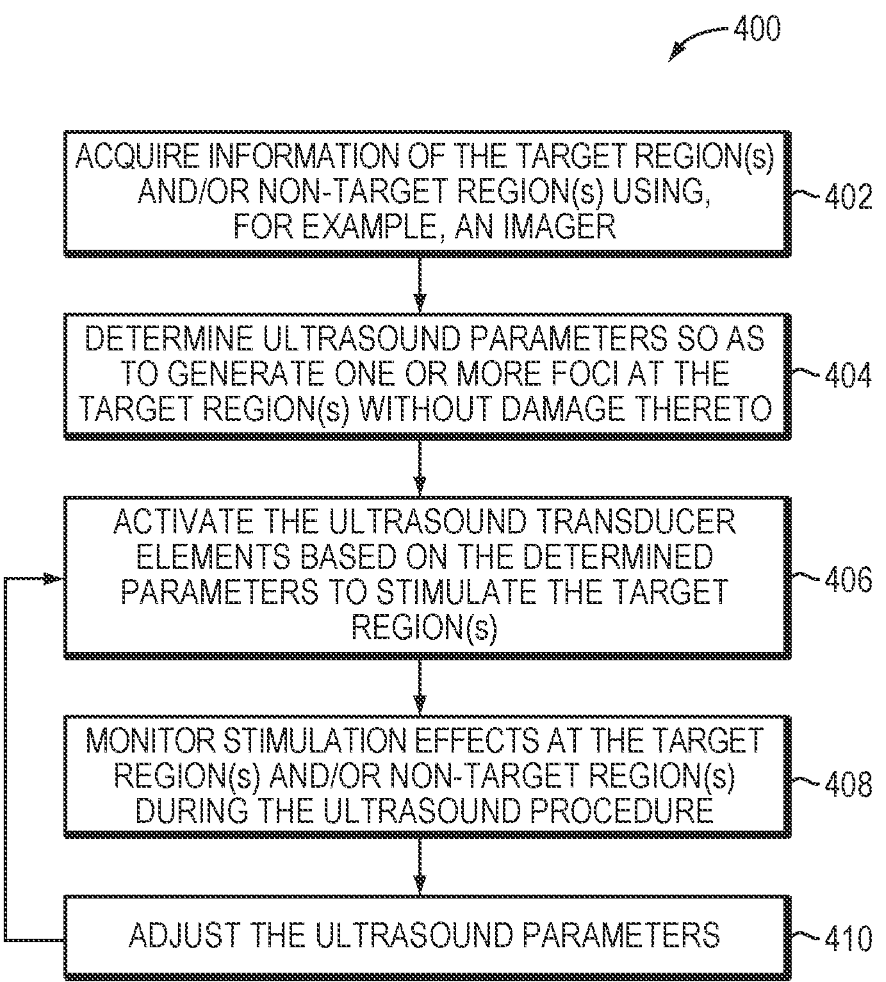
FIG. 4 is a flow chart illustrating an exemplary approach to stimulating neural activity in one or more brain regions associated with one or more diseases/disorders in accordance with various embodiments.

FIG. 4 is a flow chart illustrating an approach to stimulating neural activity in one or more brain regions associated with one or more diseases/disorders in accordance with various embodiments. In a first step 402, information (such as the location(s), anatomic characteristics and/or material characteristics) of the target region(s) and/or non-target region(s) for neurostimulation is first acquired using, for example, an imager (e.g., MRI) 122. In a second step 404, ultrasound parameters (e.g., amplitudes, phases, frequencies, steering angle(s), application duration, etc.) are determined based on the target/non-target information acquired in step 402 so as to generate one or more foci at one or more sub-regions in a target region or at one or more target regions. The multiple foci may be generated sequentially or substantially simultaneously. The acoustic pressure at the target region(s) may cause stimulation without damage thereto. For example, the temperature elevation resulting from the ultrasound may fall below a threshold corresponding to clinical significance. In a third step 406, the ultrasound transducer elements are activated based on the parameters determined in step 404. In a fourth step 408, a measuring system (e.g., fMRI, EGG, ASL MRI, fNIRS) is activated to monitor the stimulation effects (e.g., the blood flow change) at the target/non-target regions during the ultrasound procedure. In a fifth step 410, based on the measured results, ultrasound parameters are adjusted if necessary. For example, the measured results may be compared against a desired target objective determined using other approaches (e.g., conventional deep brain stimulation). If the measured results are smaller than the target objective, the amplitudes and/or durations of the sonications in the next ultrasound pulses may be increased. Additionally or alternatively, the ultrasound focus may be directed to a different sub-region of the target to enhance the neural activity. If the measured results at the target and/or non-target regions exceed the target objective, the amplitudes and/or durations of the sonications may remain unchanged or, in some embodiments, reduced to ensure safety. Steps 406-410 may be repeated until the desired target objective is achieved.

In general, functionality for stimulating neural activities in one or more sub-regions within a target region or one or more target regions associated with one or more brain diseases/disorders may be structured in one or more modules implemented in hardware, software, or a combination of both, whether integrated within a controller of the imager 122, and/or the ultrasound system 100 the administration system 124, or provided by a separate external controller or other computational entity or entities. Such functionality may include, for example, analyzing imaging data of the target and/or non-target regions acquired using the imager 122; determining the location and/or anatomic characteristics (e.g., type, property, structure, thickness, density, etc.) of the target/non-target tissue; causing the ultrasound transducer to transmit a sequence of waves/pulses/bursts to the target region(s); measuring temperature and/or a physiological parameter indicative of the neural activity at the target region(s) resulting from the ultrasound pulses/bursts; adjusting, based at least in part on the measurements, a parameter value associated with the transducer element(s); steering the focus at multiple sub-regions within the target region or at multiple target regions; dynamically grouping the transducer elements into multiple sub-arrays; causing different sub-arrays to sequentially or substantially simultaneously transmit multiple ultrasound pulse sequences to different sub-regions of the target region or different target regions; comparing the measured physiological parameter against a desired target objective; and/or iteratively performing measurements of the temperature and/or physiological parameter and adjustment of the ultrasound parameter values until the target objective is satisfied as described above.

In addition, values of the ultrasound parameters for driving the transducer elements 104 in the transducer array 102 or various sub-arrays as described above may be determined in the ultrasound controller 108, which may be separate from a control facility in the imager 122 or combined with the control facility in the imager 122 into an integrated system control facility. The controller 108 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, MATLAB, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

Further, the term "controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for stimulating neural activity in at least one target region associated with at least one brain disease or disorder using focused ultrasound, the system comprising:

an ultrasound transducer comprising a plurality of transducer elements;

an imaging device; and a controller configured to:

(a) receive an image acquired by the imaging device including the target region to identify the target region and a non-target region;

(b) transmit a first sequence of ultrasound pulses to the target region;

(c) cause real-time measurements of changes in blood flow corresponding to changes in the neural activity at the target region and the non-target region resulting from the ultrasound pulses; and (d) based at least in part on the measurements, adjust a frequency, a phase, an amplitude, or an activation duration associated with at least one of the transducer elements to cause changes in blood flow corresponding to desired changes in the neural activity at the target region and the non-target region, wherein the controller is further configured to compare the measured changes in blood flow against the desired changes in the neural activity at the target region and the non-target region and repeat steps (b)-(d) until the desired changes in neural activity are satisfied.

2. The system of claim 1, further comprising a monitoring system for measuring the changes in blood flow at the target region.

3. The system of claim 2, wherein the monitoring system comprises at least one of a fMRI, ASL MRI, EEG or fNIRS.

4. The system of claim 1, wherein the controller is further configured to:

cause the sequence of ultrasound pulses to create a focus at the target region;

cause measurements of a temperature at the focus; and based at least in part on the measured temperature, adjust a parameter value associated with at least one of the transducer elements to avoid damage to the target region.

5. The system of claim 4, wherein the controller is further configured to cause steering of the focus at a plurality of sub-regions of the target region.

6. The system of claim 4, wherein the target region is provided in plurality, and the controller is further configured to cause sequential steering of the focus at the plurality of target regions, each associated with a brain disease or disorder, different target regions associated with different brain diseases or disorders.

7. The system of claim 4, wherein the parameter value comprises at least one of a frequency, a phase, an amplitude or an activation duration.

8. The system of claim 1, wherein the ultrasound transducer comprises a plurality of sub-arrays, each sub-array comprising a plurality of transducer elements.

9. The system of claim 8, wherein the controller is further configured to cause first and second different sub-arrays of the transducer to sequentially transmit a plurality of ultrasound pulse sequences to first and second different sub-regions, respectively, of the target region.

10. The system of claim 8, wherein the controller is further configured to cause first and second different sub-arrays of the transducer to substantially simultaneously transmit a plurality of ultrasound pulse sequences to first and second different sub-regions, respectively, of the target region.

11. The system of claim 8, wherein the controller is further configured to cause first and second different sub-arrays of the transducer to sequentially transmit a plurality of ultrasound pulse sequences to first and second different target regions, respectively, wherein the first and second target regions are associated with different brain diseases or disorders.

12. The system of claim 8, wherein the controller is further configured to cause first and second different sub-arrays of the transducer to substantially simultaneously transmit a plurality of ultrasound pulse sequences to first and second different target regions, respectively, wherein the first and second target regions are associated with different brain diseases or disorders.

13. The system of claim 1, wherein the controller is further configured to:

compare the measured changes in blood flow against a target objective; and repeat steps (b)-(d) until the target objective is satisfied.

14. A method of stimulating neural activity in at least one target region associated with at least one brain disease or disorder, the method comprising:

transmitting a first sequence of ultrasound pulses from an ultrasound transducer to the target region, the ultrasound transducer comprising a plurality of transducer elements;

measuring, in real-time, changes in blood flow corresponding to changes in the neural activity at the target region and a non-target region resulting from the ultrasound pulses; and based at least in part on the measurement, adjusting a frequency, a phase, an amplitude, or an activation duration associated with at least one of the transducer elements so as to cause changes in blood flow corresponding to desired changes in the neural activity at the target region and the non-target region.

15. The method of claim 14, further comprising:

causing the sequence of ultrasound pulses to create a focus at the target region;

causing measurements of a temperature at the focus; and based at least in part on the measured temperature, adjusting a parameter value associated with at least one of the transducer elements to avoid damage to the target region.

16. The method of claim 14, wherein the ultrasound transducer comprises a plurality of sub-arrays, each sub-array comprising a plurality of transducer elements, the method further comprising causing first and second different sub-arrays of the transducer to sequentially or substantially simultaneously transmit a plurality of ultrasound pulse sequences to first and second different sub-regions, respectively, of the target region.

17. The method of claim 14, wherein the ultrasound transducer comprises a plurality of sub-arrays, each sub-array comprising a plurality of transducer elements, the method further comprising causing first and second different sub-arrays of the transducer to sequentially or substantially simultaneously transmit a plurality of ultrasound pulse sequences to first and second different target regions, respectively, wherein the first and second target regions are associated with different brain diseases or disorders.

18. The system of claim 3, wherein the monitoring system is utilized in conjunction with a blood oxygen level-dependent (BOLD) contrast agent for detecting changes in the blood flow at the target region in real time.

19. The system of claim 18, wherein the measured changes in blood flow in the target region result in a BOLD signal change detected by the monitoring system.

20. The system of claim 1, wherein the desired changes include a first change in blood flow at the target region that exceeds a first threshold.

21. The system of claim 1, wherein the desired changes further include a second change in blood flow at the non-target region that remains below a second threshold.

* * * * *